United States Patent
Stark et al.

(10) Patent No.: US 10,845,802 B2
(45) Date of Patent: Nov. 24, 2020

(54) METHOD FOR OPERATING A MOTOR VEHICLE

(71) Applicant: AUDI AG, Ingolstadt (DE)

(72) Inventors: Christiane Stark, Karlskron (DE); Isabelle Borgert, Ingolstadt (DE)

(73) Assignee: Audi AG, Ingolstadt (DE)

( * ) Notice: Subject to any disclaimer, the term of this patent is extended or adjusted under 35 U.S.C. 154(b) by 0 days.

(21) Appl. No.: 16/340,589

(22) PCT Filed: Oct. 13, 2017

(86) PCT No.: PCT/EP2017/076204
§ 371 (c)(1),
(2) Date: Apr. 9, 2019

(87) PCT Pub. No.: WO2018/137799
PCT Pub. Date: Aug. 2, 2018

(65) Prior Publication Data
US 2019/0346843 A1    Nov. 14, 2019

(30) Foreign Application Priority Data

Jan. 30, 2017    (DE) .................. 10 2017 201 405

(51) Int. Cl.
*G05D 1/00*          (2006.01)
*A61B 5/113*         (2006.01)
(Continued)

(52) U.S. Cl.
CPC ............ *G05D 1/0061* (2013.01); *A61B 5/113* (2013.01); *A61B 5/117* (2013.01); *A61B 5/18* (2013.01);
(Continued)

(58) Field of Classification Search
CPC .......... G05D 1/0061; G05D 2201/0213; A61B 5/113; A61B 5/117; A61B 5/18;
(Continued)

(56) References Cited

U.S. PATENT DOCUMENTS

2004/0044293 A1    3/2004  Burton
2006/0219459 A1*  10/2006  Suzuki .................. G08B 21/06
                                                      180/273
(Continued)

FOREIGN PATENT DOCUMENTS

CN    102407805 A    4/2012
CN    102768708 A   11/2012
(Continued)

OTHER PUBLICATIONS

International Preliminary Report on Patentability directed to related International Patent Application No. PCT/EP2017/076204, completed Jan. 9, 2019, with attached English-language translation; 11 pages.

(Continued)

*Primary Examiner* — Sze-Hon Kong
(74) *Attorney, Agent, or Firm* — Sterne, Kessler, Goldstein & Fox P.L.L.C.

(57) ABSTRACT

The present disclosure relates to a method for operating a motor vehicle. At least one breathing movement parameter describing an upper body movement of a user of the motor vehicle and a driving movement parameter are detected, using a sensor device of the motor vehicle, and a breathing signal and a driving movement signal that describe how the parameters are generated. A vitality parameter that describes breathing of the user is determined on the basis of the signals. An evaluation and control device of the motor vehicle ascertains a reference value range of stored, user-specific reference values of the vitality parameter, a deter- (Continued)

mined value of the vitality parameter lying in said range, and, on the basis of the ascertained reference value range, a driver state index is determined. A control signal for operating a driver assistance device of the motor vehicle is generated as a function of the determined driver state index.

21 Claims, 2 Drawing Sheets

(51) Int. Cl.
    *A61B 5/117*     (2016.01)
    *A61B 5/18*     (2006.01)
    *A61B 5/00*     (2006.01)
    *B60K 28/02*     (2006.01)
    *B60W 40/08*     (2012.01)

(52) U.S. Cl.
    CPC .......... *A61B 5/6893* (2013.01); *A61B 5/7221* (2013.01); *B60K 28/02* (2013.01); *B60W 40/08* (2013.01); *B60W 2040/0872* (2013.01); *B60W 2520/00* (2013.01); *B60W 2540/22* (2013.01); *B60W 2556/00* (2020.02); *B60Y 2200/11* (2013.01); *B60Y 2302/00* (2013.01); *G05D 2201/0213* (2013.01)

(58) Field of Classification Search
    CPC .... A61B 5/6893; A61B 5/7221; B60K 28/02; B60W 40/08; B60W 2556/00; B60W 2040/0872; B60W 2520/00; B60W 2540/22; B60Y 2200/11; B60Y 2302/00
    See application file for complete search history.

(56) References Cited

U.S. PATENT DOCUMENTS

| | | | | |
|---|---|---|---|---|
| 2006/0283652 | A1* | 12/2006 | Yanai | G08B 21/06 180/272 |
| 2010/0063365 | A1* | 3/2010 | Pisani | A61B 5/0002 600/301 |
| 2011/0224875 | A1 | 9/2011 | Cuddihy et al. | |
| 2012/0078122 | A1 | 3/2012 | Yokoyama et al. | |
| 2012/0256749 | A1 | 10/2012 | Rao et al. | |
| 2014/0097957 | A1 | 4/2014 | Breed et al. | |
| 2014/0276090 | A1 | 9/2014 | Breed | |
| 2015/0265200 | A1 | 9/2015 | Mahdi et al. | |
| 2016/0001781 | A1* | 1/2016 | Fung | G16H 50/20 701/36 |
| 2016/0294707 | A1 | 10/2016 | Chen | |
| 2016/0345907 | A1* | 12/2016 | Fung | A61B 5/6893 |
| 2017/0140232 | A1* | 5/2017 | Banno | A61B 5/1114 |
| 2017/0161576 | A1* | 6/2017 | Banno | G06K 9/00281 |
| 2017/0305349 | A1* | 10/2017 | Naboulsi | B60R 1/025 |
| 2017/0309089 | A1* | 10/2017 | Shimada | B60W 40/10 |
| 2017/0368936 | A1* | 12/2017 | Kojima | B60K 28/06 |
| 2018/0176741 | A1* | 6/2018 | Cremer | G01C 21/26 |
| 2018/0201274 | A1* | 7/2018 | Matsumura | G06K 9/00845 |
| 2018/0319279 | A1* | 11/2018 | Ikeda | G06K 9/00845 |
| 2019/0061772 | A1* | 2/2019 | Prinz | A61B 5/747 |
| 2019/0110729 | A1* | 4/2019 | Yamataka | B60W 30/182 |
| 2019/0290180 | A1* | 9/2019 | Kusukame | A61B 5/026 |
| 2019/0376794 | A1* | 12/2019 | Cremer | G06F 16/9537 |

FOREIGN PATENT DOCUMENTS

| | | |
|---|---|---|
| CN | 104898834 A | 9/2015 |
| CN | 105476647 A | 4/2016 |
| DE | 102004016191 A1 | 9/2005 |
| DE | 102005059687 A1 | 6/2007 |
| DE | 102009053407 A1 | 6/2010 |
| DE | 102011113100 A1 | 3/2013 |
| DE | 102015002968 A1 | 8/2015 |
| DE | 102014204340 A1 | 9/2015 |
| DE | 102014211501 A1 | 9/2015 |
| JP | 2009213636 A | 9/2009 |
| JP | 2016220816 A | 12/2016 |
| WO | WO-2015/127193 A1 | 8/2015 |
| WO | WO-2015140273 A2 | 9/2015 |
| WO | WO-2015174963 A1 | 11/2015 |
| WO | WO-2015/200224 A2 | 12/2015 |

OTHER PUBLICATIONS

International Search Report and Written Opinion of the International Searching Authority directed to related International Patent Application No. PCT/EP2017/076204, dated Jan. 5, 2018, with attached English-language translation; 21 pages.

* cited by examiner

METHOD FOR OPERATING A MOTOR VEHICLE

TECHNICAL FIELD

The present disclosure relates to a method for operating a motor vehicle and to a motor vehicle. The motor vehicle has a sensor device for detecting at least one breathing parameter describing an upper body movement of a user of the motor vehicle and for detecting a driving movement parameter describing a movement of a motor vehicle seat of the motor vehicle.

BACKGROUND

In modern motor vehicles, monitoring systems are provided to improve driving safety. Monitoring systems of this type can determine and/or detect physiological parameters of the user, known as vitality parameters, during travel, and determine therefrom for example a fitness of the user to drive.

DE 10 2015 002 968 A1 takes into account for example a travel distance or a time of day or a fuel consumption in assessing the driver state.

DE 10 2009 053 407 A1 proposes detecting for example a frequency of a heartbeat or a breathing frequency of the vehicle occupant. According to WO 2015/140273 A2, an acceleration sensor is integrated into the safety belt so as to be able to infer the heart activity or breathing.

DE 10 2004 016 191 A1 describes for this purpose a technology in which, for detecting the breathing frequency, a movement sensor is integrated into a safety belt and detects a movement of a ribcage of the user or of the stomach. In the signal analysis, the breathing frequency and/or heart frequency are thus filtered out and derived.

Detecting a breathing movement of the user by means of a sensor device arranged on the safety belt is also proposed by DE 10 2005 059 687 A1, a tension-sensitive element measuring an expansion of the ribcage. A correction unit is provided that takes a vehicle movement into account in determining the breathing frequency.

US 2004/0044293 A1 describes a system for monitoring alertness or wakefulness of a user of a motor vehicle using a value that describes a breathing state.

First, detecting vitality parameters for example during a journey has the application of simply providing the driver with information regarding his state. Other systems also incorporate a medical aspect, and monitor the vitality parameters of the user so as for example to trigger an emergency call in emergency situations. In recently developed motor vehicles, however, a new aspect comes into play, since modern motor vehicles are often equipped with driver assistance systems that can be operated in fully autonomous driving modes. In these motor vehicles that drive in a piloted manner, it may occur that the motor vehicle cedes control to the user. However, since the user can dedicate himself to other activities during the fully autonomous or piloted driving mode, there may be situations in which the motor vehicle provides a handover of control to the user, but the user is not very alert at this moment or it would be better for him not to take over control at this moment.

BRIEF DESCRIPTION OF THE DRAWINGS/FIGURES

DETAILED DESCRIPTION

Figure 1:
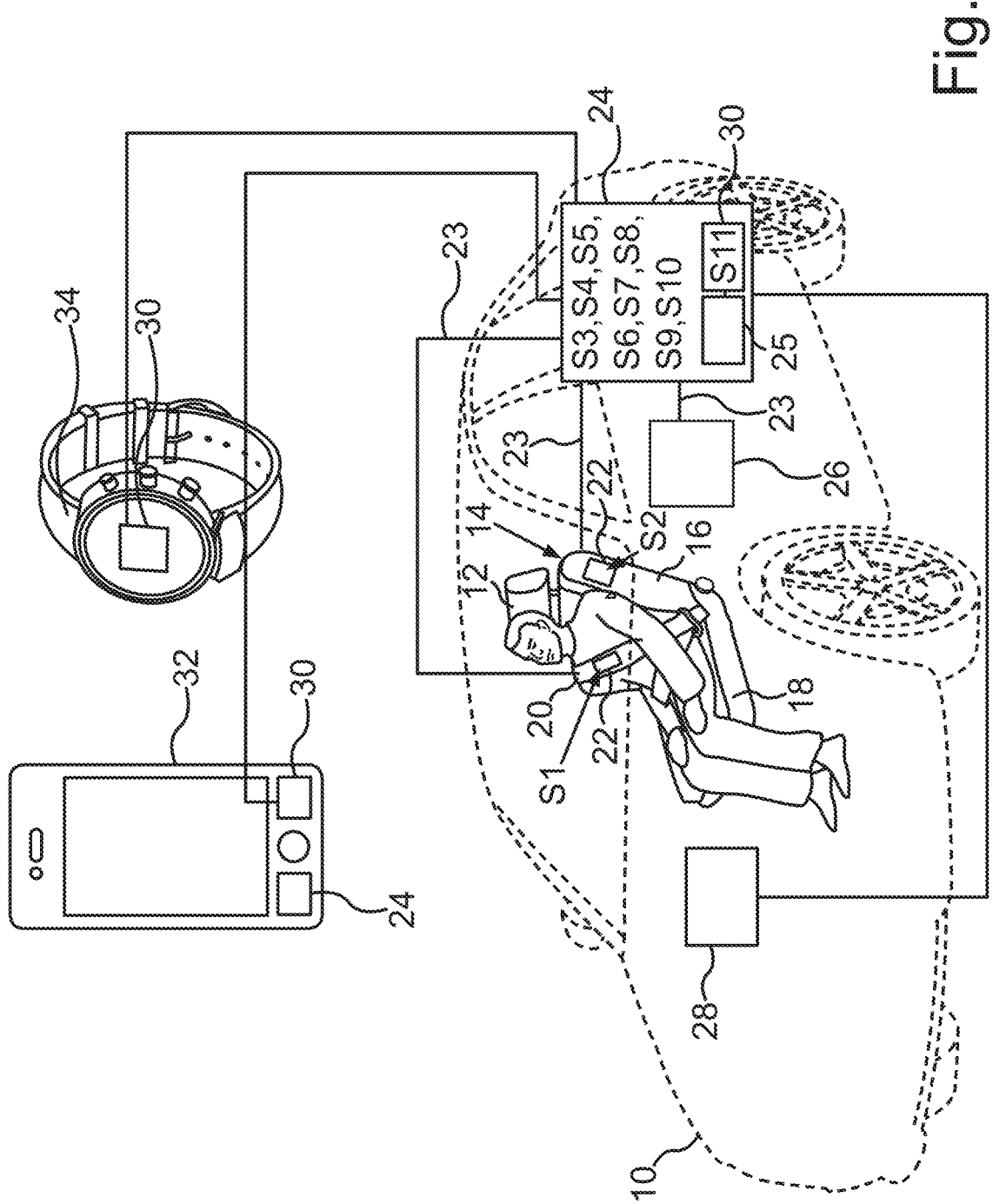
FIG. 1 illustrates a schematic drawing of a method, according to some embodiments.

An object of the present disclosure is situation-dependent optimization of a handover of control of a motor vehicle.

The object is achieved by a method according to some embodiments and the subject matter according to some embodiments of the coordinated claims. Further advantageous embodiments are set out by the dependent claims.

Some embodiments are based on the idea of determining in a user-specific manner whether a current situation is a favorable moment for the vehicle handover. For this purpose, not only is a pure numerical value of the vitality parameter taken into account, but it is checked whether the current value of the parameter is a value that is in a normal value range for the individual user or for example constitutes a critical value for this person.

The method according to some embodiments for operating a motor vehicle comprises the following method steps.

At least one breathing movement parameter describing an upper body movement of a user of the motor vehicle is generated and a breathing movement signal describing the detected breathing movement parameter is generated, using a sensor device of the motor vehicle. A driving movement parameter describing a movement of a motor vehicle seat of the motor vehicle is detected and a driving movement signal describing the detected driving movement parameter is generated, also using the sensor device. In this context, a sensor device is understood to be an apparatus or an apparatus component that is set up for the method steps in question and for this purpose has, for example, one or more sensors. For detecting the upper body movement, for example, a movement sensor or an acceleration sensor may be arranged in a seatbelt of the motor vehicle. For detecting the movement of the motor vehicle seat, for example, a further movement sensor or a further acceleration sensor may be arranged in a seat cushion of the motor vehicle.

A vitality parameter, in other words a physical parameter that describes breathing of the user, is determined on the basis of the breathing movement signal and the driving movement signal, using an analysis and control device, in other words an appliance or an appliance component for electronic data processing and for generating control signals. In this context, the vitality parameter may, for example, be a breathing depth and/or a breathing frequency. The analysis and control device may for example be configured as a control appliance or a control circuit board.

For determining the vitality parameter, a value described by the breathing movement signal is normalized on the basis of a value of the driving movement signal, for example, in that, on the basis of the driving movement signal, an influence of the movement of the motor vehicle seat on the detected breathing movement parameter and/or on the first sensor device is determined.

Subsequently, on the basis of the determined influence, the value of the breathing movement parameter can be adapted, for example. In other words, an upper body movement that results not from the actual breathing but rather from a movement of the vehicle or of the motor vehicle seat is filtered out or removed from the calculation, in such a way that the value of the vitality parameter only describes the movement actually made as a result of the user's breathing.

In the method according to some embodiments, a reference value range, in which a determined value of the vitality parameter lies, is ascertained. In this context, the reference value range comprises user-specific reference values of the vitality parameter that are stored in a storage device. A storage device is understood to be a part or an appliance component that is configured for electronic data storage and, for example, may be configured as a hard disk or memory card. For example, it is also possible for a plurality of reference value ranges to be stored in the storage device, from which a reference value range can subsequently be selected.

On the basis of the ascertained reference value range, a driver state index is ascertained that describes a current physiological state of the user. In other words, a different driver state index, which may describe, for example, a degree of alertness or tiredness or a degree of a stress state of the user, may be assigned to the reference value range or to each of a plurality of reference value ranges, for example, in an electronically stored list.

A control signal for operating a driver assistance device of the motor vehicle is generated and the control signal is transmitted to the driver assistance device, using the analysis and control device, as a function of the determined driver state index.

The driver assistance device can subsequently for example break off or continue a currently set driving mode as a function of the determined driver state index. In this context, the driver assistance device is an appliance or a part that is set up and configured to operate the motor vehicle in one or more driving modes, and may, for example, be a conventional driver assistance system of the motor vehicle.

As a result of the method according to some embodiments, the aforementioned drawbacks are reduced or even overcome. The vitality parameter relating to breathing is particularly well-suited for analyzing the driver state, since the driver state can be described very reliably. Because the driver state index is only determined by comparison with the user-specific reference value range, it is possible to distinguish between different users who may for example be of a different bodily or sporting constitution. Therefore, a reliable decision can be made as to whether, for example, the driver can reliably and rapidly take over the motor vehicle at the moment.

For example, a competitive athlete generally has a very high lung volume and therefore slower breathing than an unexercised user of the motor vehicle. A value for example of a breathing depth, which may be in a normal range and indicate a normal, relaxed but wakeful and concentrated bodily state for a competitive athlete, may be a sign of high tiredness or in some cases that the user is even asleep for a user who rarely does sports.

If, for example, the breathing depth is measured as a vitality parameter, in other words an expansion of the ribcage and/or stomach of the user, a prediction as to a lung volume, for example, how much oxygen can be taken up by the user in one breath, can be made using the comparison with the reference value range. Shallow, rapid breathing may, for example, be a normal state for a first user, whilst in another user this may already be a sign of stress. By means of the method according to some embodiments, however, individual differences of this type can be recognized.

Using the method according to some embodiments, the parameters are recorded in an identical manner, in other words simultaneously and using related technologies. As a result, the detection of the vitality parameter is particularly reliable. The method according to some embodiments makes possible a comprehensive driving state analysis, for example, by identifying breathing patterns.

In some embodiments of the method, an identity of the user is ascertained using the analysis and control device, for example, on the basis of state data, which the user can specify when the motor vehicle is started, or for example, by detecting a biometric feature of the user or an identification code, for example, of a motor vehicle key. The user-specific reference values of the vitality parameter are provided and the reference value range ascertained as a function of the ascertained identity. The method according to some embodiments can thus be used for different users, and as a result the operation of the motor vehicle is even better personalized and is very flexible.

It may be provided that at least one vitality parameter signal is received, which may describe a value of the vitality parameter or of a further vitality parameter, for example, a value that can describe a pulse of the user. The vitality parameter signal may be received from a portable accessory and/or from a mobile terminal. The driver state index can subsequently be ascertained as a function of the received vitality parameter signal. Using this variant of the method according to some embodiments, it is possible additionally to use, for example, historical vitality parameters that the user has, for example, gathered outside the motor vehicle, and the prediction as to the driver state can thus be refined even better.

Some embodiments of the method have the same advantage, and are characterized by receiving at least one operating signal from a motor vehicle system, which can describe an operating state of the motor vehicle system. The driver state index is subsequently ascertained as a function of the received operating signal. In other words, sensor information from the vehicle sensor system can be used, and the driver state can also be inferred therefrom. For example, in this way a setting of an air conditioning system to an unusually high temperature can give an indication that the user may for example be stressed or ill.

So as to "get to know" the user better, in other words so as to refine and personalize the method according to some embodiments more and more over time, it may be provided that the detected value of the vitality parameter is stored as a reference value in the storage device and that the reference value range is adapted as a function of the stored value. These optional method steps may also be carried out by the analysis and control device.

The object set above is also achieved by an analysis and control device, which may comprise a microcontroller and/or a microprocessor, the analysis and control device being set up to carry out the method steps relating to an analysis and control device in accordance with a method according to one of the above-disclosed embodiments. This results in the aforementioned advantages.

The object is also solved, in such a way as to achieve the aforementioned advantages, by a motor vehicle comprising a driver assistance device and a sensor device, the sensor device comprising a sensor for detecting the breathing movement parameter describing the upper body movement of the user of the motor vehicle and a sensor for detecting the driving movement parameter describing the movement of the motor vehicle seat. The motor vehicle according to some embodiments is characterized by an embodiment of the analysis and control device, and may, for example, be configured as a motorcar, for example, as a passenger motorcar.

In this context, the sensor for detecting the breathing movement parameter may be arranged on a safety belt of the motor vehicle, and the sensor for detecting the driving movement parameter may be arranged on a motor vehicle seat. As a result, the corresponding parameters can be detected particularly well.

The advantages are also achieved by a storage device comprising a program code that is set up to carry out a method according to one of the above-described embodiments when executed by an analysis and control unit of a mobile terminal.

Some embodiments also relate to a mobile, portable terminal comprising a storage device according to some embodiments and a server device for operating online, comprising a storage device according to some embodiments. Hereinafter, some embodiments are described.

The described components of an embodiment each constitute individual features of some embodiments, which are to be considered mutually independently, and which also develop some embodiments mutually independently and are thus also to be considered part of some embodiments individually or in a combination other than that disclosed. Further, the described embodiments can also be supplemented with further ones of the already described features of some embodiments.

In the drawings, functionally equivalent elements are provided with like reference numerals in each case.

FIG. 1 describes the principle behind a method, according to some embodiments. For this purpose, FIG. 1 shows a motor vehicle 10 of a user 12. The motor vehicle 10 may, for example, be configured as a passenger motorcar. The user 12 sits on a motor vehicle seat 14 comprising a backrest 16, a seat cushion 18 and a safety belt 20.

The motor vehicle 10 also comprises a sensor device 22, which may, for example, comprise two sensors, it being possible for one of the sensors to be arranged on the safety belt 20 and the other of the sensors to be arranged on the motor vehicle seat 14. The sensor for detecting the breathing movement parameter may, for example, be glued onto the safety belt 20 or sewn into the safety belt 20. The sensor for detecting the driving movement parameter may, for example, be integrated into the backrest 16 or into the seat cushion 18. However, alternative variants are also conceivable in this context, for example, a plurality of sensors both in the backrest 16 and in the seat cushion 18.

The sensor for detecting the breathing movement parameter may, for example, be a sensor known from the prior art for detecting an acceleration and/or a movement and/or a shock. Likewise, the sensor for detecting the driving movement parameter may, for example, be a movement and/or acceleration sensor. The sensor for detecting the driving movement parameters may, for example, detect a resonant vibration of the motor vehicle seat 14.

The sensor for detecting the breathing movement parameter may, for example, detect a three-dimensional movement for measuring a breathing depth and/or a breathing movement. Depending on the application, this sensor may be arranged at a suitable point on the safety belt 20, for example, at a point where the safety belt 20 lies on a chest center-point of the user 12 or on the stomach of the user 12. Since the movements of the motor vehicle seat 14 act on the body of the user 12, not only the movements of the upper body that are caused by breathing are detected by the first sensor, but rather the entire movement of the upper body.

The sensor device 22 may be connected via a data communications link 23 to an analysis and control device 24. A data communications link 23 of this type may, for example, be a wired data communications connection, for example, a component of a data bus system of the motor vehicle 10, or a wireless data communications link, such as a WLAN or Bluetooth LE connection.

The analysis and control device 24 may, for example, be configured as a control device of the motor vehicle 10, as a software module or as a control circuit board. The analysis and control device 24 may optionally comprise a microcontroller 25 and/or a microprocessor 25. The analysis device may comprise a storage device 30, which may be configured, for example, as a storage medium, for example, as a data store and/or hard disk. The storage device 30 and the microcontroller 25 or microprocessor 25 can communicate with one another. Optionally, the microprocessor 25 or the microcontroller 25 may have access to a program code stored in the storage device 30, the program code being set up to carry out an embodiment of the method according to the invention when executed by the analysis and control device.

The motor vehicle 10 also comprises a driver assistance device 26, which may, for example, be configured as a driver assistance system that is familiar in the prior art to a person skilled in the art and that may, for example, be set up to operate the motor vehicle 10 in a piloted driving mode.

FIG. 1 also shows a motor vehicle system 28 of the motor vehicle 10, which may be configured, for example, as an air conditioning system or steering system or infotainment system.

The example of FIG. 1 also shows a portable mobile terminal 32, which may be configured, for example, as a smartphone. In this context, FIG. 1 shows that the analysis and control device 24 need not be arranged in the motor vehicle 10, but rather may also alternatively be part of the mobile, portable terminal 32. However, the corresponding data communications links, which may be wireless data communications links, are not shown for this variant in FIG. 1 for reasons of clarity.

Finally, FIG. 1 shows a portable accessory 34, which may, for example, be configured as a wristwatch or fitness belt and may also be referred to as a "wearable".

In a first method step S1, the sensor device 22 detects the breathing movement parameter and generates a corresponding sensor signal that describes the detected breathing parameter. For example, the sensor device 22 detects a 3-dimensional movement or a pressure. Simultaneously, the sensor of the sensor device 22 can detect a shock or resonant vibration of the motor vehicle seat 14 and generate a corresponding driving movement signal (S2) that describes this resonant movement or shock. The individual sensors transmit the respective signals to the analysis and control device 24.

Since a shock of the motor vehicle seat and, for example, a simultaneous expansion of the ribcage add together, and the breathing movement signal thus describes the total of all effects on the sensor in the safety belt 20, in method step S3 the analysis and control device 24 determines a normalized value of the breathing movement, for example, the actual breathing depth and/or the breathing movement actually caused merely by the ribcage. For this purpose, for example, the value of the driving movement signal can be subtracted from the value of the breathing movement parameter.

In the storage device 30, for example, a plurality of reference values of the user 12 may be stored, and may, for example, be classified into a plurality of reference value ranges. In this context, a level of the vitality parameter, for example, may be assigned to each of the reference value ranges, in other words to a predetermined driver state. In the example of FIG. 1, the motor vehicle 10 may, for example, be used regularly by different users 12, for example, by a competitive athlete and by a user 12 who has a normally conventional constitution. So as to be able to respond to the current user 12 in a more individual manner, according to the method it may be provided that, for example, when the motor vehicle 10 is opened or when the motor vehicle 10 is started an identification process is carried out in which an identity of the user 12 is ascertained (S4).

For ascertaining the identity (S4), for example, an identification code of a motor vehicle key or, for example, a PIN that the user 12 may have entered before the start-up of the motor vehicle 10 may be queried. If the analysis and control device 24, for example, ascertains (S4) that the competitive athlete is now using the motor vehicle 10, the reference values of the vitality parameter that are stored, for example, for his user profile may be provided (S5). In accordance with the ascertained identity, classification into reference value ranges may also take place, or the corresponding reference value ranges may be ascertained (S6). In this context, the classification of the reference values into the reference value ranges may already be provided in a user-specific manner.

For example, the determined vitality parameter may describe very slow breathing. Whilst a corresponding value of the vitality parameter may be a sign of, for example, tiredness for the normally exercised user 12, the reference values of the competitive athlete may describe, for example, that this is a normal value for this user 12 in an alert state of wakefulness. In method step S7, it may also be ascertained that the user 12 is wakeful at the moment.

In the example situation of FIG. 1, the motor vehicle 10 may, for example, be approaching a road portion in which piloted driving is not allowed. For example, on the basis of map data the driver assistant device 26 may detect that it is advisable beforehand to hand over control of the motor vehicle 10 to the user 12. Since the user 12 is wakeful and alert at the moment, the analysis and control device 24 may generate a control signal (S8) that can describe a handover of this type and thus a breakoff of the piloted driving mode. In method step S9, the control signal is subsequently transmitted to the driver assistance device 26. Thereupon, the driver assistance device 26 may, for example, inform the user 12 as to the coming change in command and subsequently change the piloted driving mode. Alternatively, if the other user 12 is in the motor vehicle 10, whose driver state index may, for example, describe that there is a high probability that he is tired and therefore less alert at the moment, it may, for example, be appropriate to brake the motor vehicle 10 and, for example, park it at a roadside, and only then to end the piloted driving mode.

FIG. 1 schematically shows further variants with which the method according to some embodiments can be refined. For example, the determined vitality parameter may be taken as a reference value. Alternatively or in addition, a vitality parameter, including a vitality parameter of a different type such as a pulse or a vitality parameter relating to heart activity, may, for example, be received from the storage device 30 of the portable accessories 34 and/or from the storage device 30 of the mobile terminal 32 (S10). These data may be included in the process of ascertaining the driver state index (S7). Alternatively or in addition, these vitality parameters may be stored in the storage device 30 of the analysis and control device 24 of the motor vehicle 10 as a reference value (S11). As the number of reference values increases, a standard bandwidth can be set, leading to unerring detection of the current state of the user.

Alternatively or in addition, for example, operating signals from the motor vehicle system 28 or a plurality of motor vehicle systems 28 may be analyzed, and are also received by the analysis and control device 24 (S10). In this context, the behavior of the user 12 motor vehicle 10 can thus be analyzed.

Optionally, it may be provided that the driver state index can be transmitted, for example, to a comfort system 28 or that the analysis and control device 24 can generate a control signal for operating the comfort system 28 and transmit it to the comfort system 28. Thus, for example, in accordance with the state of the driver, the air conditioning system may be regulated, or a suggestion may first be made to the user 12 as to whether he might wish for example to reduce a temperature or, for example, to change an internal lighting.

Figure 2:
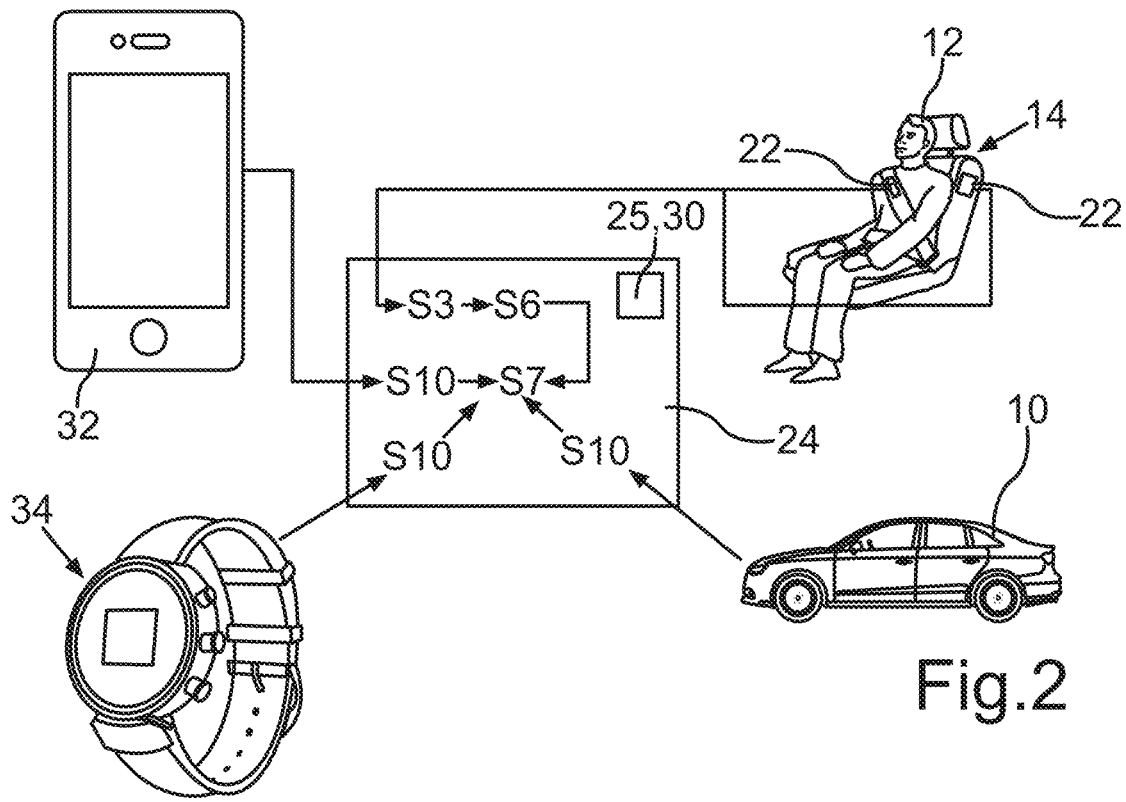
FIG. 2 illustrates a schematic drawing of a method, according to some embodiments.

FIG. 2 schematically shows a further embodiment of the method according to some embodiments, only the differences from the method of FIG. 1 being discussed hereinafter.

In this context, FIG. 2 again illustrates the possible data by means of which the driver state index can be ascertained (S7). In addition to the data of the sensor device 22, vehicle data of the motor vehicle 10 may be included in the driver state index, for example, data regarding a steering movement. Optionally, further values relating to the vitality parameter or values of the other vitality parameter may be included in the driver state index, for example, annual and/or current vitality values from a portable accessory 34. Alternatively or in addition, however, it is also conceivable for these other values of vitality parameters to be detected by the motor vehicle 10, for example, by means of an impulse sensor on the steering wheel. Vitality parameters may optionally be received from the mobile terminal 32 (S10), for example, what are known as "shared values" of a vitality parameter or "shared vitality values", for example, historical data that were saved, for example, by a user program of the mobile terminal 32 over a relatively long time period.

Figure 3:
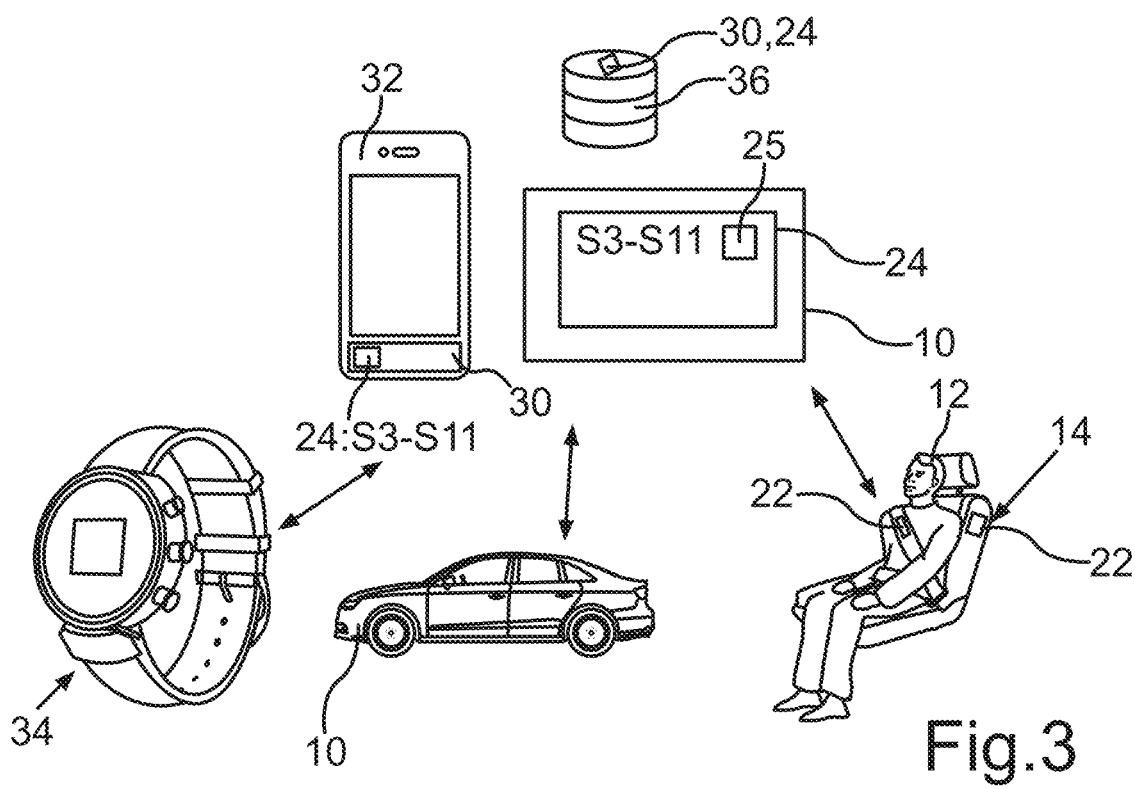
FIG. 3 illustrates a schematic drawing of a method, according to some embodiments.

FIG. 3 illustrates different modules by means of which the method steps relating to the analysis and control device 24 can be carried out, according to some embodiments. As well as the variant described in relation to FIG. 1, in which an analysis and control device 24 of the motor vehicle 10 can carry out the method according to some embodiments, the method may alternatively be carried out by an analysis and control device 24 of the mobile terminal 32 or an analysis and control device 24 of a server device 36 external to the motor vehicle. In the module in question, in other words in the appliance in question, a data fusion described by the method according to some embodiments may take place.

Overall, the embodiments illustrate how the method according to some embodiments makes driver state monitoring possible, for example, in relation to piloted driving phases in which it is important to monitor the readiness for example of a driver to take on the task of driving again.

In some embodiments, the person in a motor vehicle seat 14 can be identified in advance, for example, by a suitable method, for example by way of a vehicle key and/or a smartphone and/or a wearable. In other words, the identity of the user 12 can be ascertained (S4). This is important for unambiguous assignment of the data to a particular user 12, for example, so as to identify "normal states" and states deviating therefrom, such as stress or fatigue, using learning algorithms.

This takes place through the use of, for example, two suitable sensors of the sensor device 22, which measure a movement, for example, the breathing movement, shock and acceleration, for example, in an identical manner, in other words simultaneously and using identical or similar technology. In this context, a first sensor may, for example, be located at chest height to a safety belt 20, and a control sensor may be attached at any suitable point in the vehicle seat 14 where it cannot be influenced by movements of the user 12.

A breathing frequency and/or a breathing depth can now be detected as follows: The two example sensors can send the measurement results thereof to the analysis and control device 24, for example, to a receiver unit of the analysis and control device 24, which can analyze the data. In this context, the first sensor may detect both the movement data and/or shock data and/or acceleration data generated by the vehicle and the movements generated by the human.

The control sponsor can now detect only the movement data and/or shock data and/or acceleration data generated by the motor vehicle (S2).

The data detected by the first sensor and by the control sensor may be compared, for example, in the receiver unit. The comparison results in the data that are generated purely by the human, from which breathing frequency and/or depth are determined (S3).

The analysis and control device 24, for example, by means of the receiver unit, can in turn pass the data on breathing frequency and/or breathing depth to, for example, a control appliance and/or software module of the analysis and control device 24, which by means of learning algorithms give a comparison between normal breathing frequency and/or breathing depth of the user 12 and any deviating states such as stress (e.g., rapider, shallower breathing) and fatigue (e.g., slower, deeper breathing).

In the example control appliance, the data on breathing frequency and/or breathing depth may optionally be processed together with other sensor information from vehicle sensors and/or additionally from a portable accessory worn by the user 12, to form a driver state index (S7), which can in turn go to the relevant motor vehicle systems 28 (e.g., comfort and/or safety).

The invention claimed is:

1. A method for operating a motor vehicle, comprising:
   detecting, using a first sensor of a sensor device, a breathing movement parameter describing an upper body movement of a user of the motor vehicle, wherein the first sensor is arranged on a safety belt of the motor vehicle;
   generating, using the first sensor of the sensor device, a breathing movement signal describing the detected breathing movement parameter;
   detecting, using a second sensor of the sensor device, a driving movement parameter describing a movement of a motor vehicle seat of the motor vehicle;
   generating, using the second sensor of the sensor device, a driving movement signal describing the detected driving movement parameter;
   determining, using an analysis and control device, a value of a vitality parameter based on the breathing movement signal and the driving movement signal by normalizing a value described by the breathing movement signal based on a value of the driving movement signal, wherein the vitality parameter describes breathing of the user;
   ascertaining, using the analysis and control device, a reference value range in which the determined value of the vitality parameter lies, wherein the reference value range comprises user-specific reference values of the vitality parameter that are stored in a storage device;
   ascertaining, using the analysis and control device, a driver state index describing a current physiological state of the user based on the ascertained reference value range;
   generating, using the analysis and control device, a control signal for operating a driver assistance device of the motor vehicle based on the ascertained driver state index; and
   transmitting, using the analysis and control device, the control signal to the driver assistance device.

2. The method of claim 1, further comprising:
   ascertaining, the analysis and control device, an identity of the user;
   providing, by the analysis and control device, the user-specific reference values of the vitality parameter; and
   ascertaining, by the analysis and control device, the reference value range based on the ascertained identity.

3. The method of claim 1, further comprising:
   receiving, by the analysis and control device, a vitality parameter signal that describes the value of the vitality parameter or a value of another vitality parameter from a portable accessory or a mobile terminal; and
   wherein the ascertaining, by the analysis and control device, the driver state index further comprises ascertaining, by the analysis and control device, the driver state index based on the received vitality parameter signal.

4. The method of claim 1, further comprising:
   receiving, by the analysis and control device, an operating signal from a motor vehicle system, wherein the operating signal describes an operating state of the motor vehicle system; and
   wherein the ascertaining, by the analysis and control device, the driver state index further comprises ascertaining, by the analysis and control device, the driver state index based on the received operating signal.

5. The method of claim 1, further comprising:
   storing, by the analysis and control device, the determined value of the vitality parameter as a reference value in the storage device; and
   adapting, by the analysis and control device, the reference value range based on the stored reference value.

6. An analysis and control device, comprising:
   a microcontroller or a microprocessor configured to:
      determine a value of a vitality parameter based on a breathing movement signal and a driving movement signal by normalizing a value described by the breathing movement signal based on a value of the driving movement signal, wherein the vitality parameter describes breathing of a user;
      ascertain a reference value range in which the determined value of the vitality parameter lies, wherein the reference value range comprises user-specific reference values of the vitality parameter that are stored in a storage device;
      ascertain a driver state index describing a current physiological state of the user based on the ascertained reference value range;
      generate a control signal for operating a driver assistance device of a motor vehicle based on the ascertained driver state index; and
      transmit the control signal to the driver assistance device.

7. A motor vehicle, comprising:
   a driver assistance device;
   a sensor device comprising a first sensor arranged on a safety belt of the motor vehicle and a second sensor arranged on a motor vehicle seat of the motor vehicle, wherein the first sensor is configured to detect a breathing movement parameter describing an upper body movement of a user of the motor vehicle; and wherein the second sensor is configured to detect a driving movement parameter describing a movement of the motor vehicle seat; and an analysis and control device configured to:
determine a value of a vitality parameter based on a breathing movement signal and a driving movement signal by normalizing a value described by the breathing movement signal based on a value of the driving movement signal, wherein the vitality parameter describes breathing of the user;
ascertain a reference value range in which the determined value of the vitality parameter lies, wherein the reference value range comprises user-specific reference values of the vitality parameter that are stored in a storage device;
ascertain a driver state index describing a current physiological state of the user based on the ascertained reference value range;
generate a control signal for operating a driver assistance device of the motor vehicle based on the ascertained driver state index; and
transmit the control signal to the driver assistance device.

8. The motor vehicle of claim 7, wherein the analysis and control device is further configured to:
ascertain an identity of the user;
provide the user-specific reference values of the vitality parameter; and
ascertain the reference value range based on the ascertained identity.

9. The motor vehicle of claim 7, wherein the analysis and control device is further configured to:
receive a vitality parameter signal that describes the value of the vitality parameter or a value of another vitality parameter from a portable accessory or a mobile terminal; and
wherein to ascertain the driver state index, the analysis and control device is further configured to ascertain the driver state index based on the received vitality parameter signal.

10. The motor vehicle of claim 7, wherein the analysis and control device is further configured to:
receive an operating signal from a motor vehicle system, wherein the operating signal describes an operating state of the motor vehicle system; and
wherein to ascertain the driver state index, the analysis and control device is further configured to ascertain the driver state index based on the received operating signal.

11. The motor vehicle of claim 7, wherein the analysis and control device is further configured to:
store the determined value of the vitality parameter as a reference value in the storage device; and
adapt the reference value range based on the stored reference value.

12. A storage device of a mobile portal terminal comprising a program code that when executed by an analysis and control unit of the mobile portal terminal, causes the analysis and control unit to perform operations comprising:
determining a value of a vitality parameter based on a breathing movement signal and a driving movement signal by normalizing a value described by the breathing movement signal based on a value of the driving movement signal, wherein the vitality parameter describes breathing of a user;
ascertaining a reference value range in which the determined value of the vitality parameter lies, wherein the reference value range comprises user-specific reference values of the vitality parameter that are stored in the storage device;
ascertaining a driver state index describing a current physiological state of the user based on the ascertained reference value range;
generating a control signal for operating a driver assistance device of a motor vehicle based on the ascertained driver state index; and
transmitting control signal to the driver assistance device.

13. The storage device of claim 12, wherein the operations further comprise:
ascertaining an identity of the user;
providing the user-specific reference values of the vitality parameter; and
ascertaining the reference value range based on the ascertained identity.

14. The storage device of claim 12, wherein the operations further comprise:
receiving a vitality parameter signal that describes the value of the vitality parameter or a value of another vitality parameter from a portable accessory or a mobile terminal; and
wherein the ascertaining the driver state index further comprises ascertaining the driver state index based on the received vitality parameter signal.

15. The storage device of claim 12, wherein the operations further comprise:
receiving an operating signal from a motor vehicle system, wherein the operating signal describes an operating state of the motor vehicle system; and
wherein the ascertaining the driver state index further comprises ascertaining the driver state index based on the received operating signal.

16. The storage device of claim 12, wherein the operations further comprise:
storing the determined value of the vitality parameter as a reference value in the storage device; and
adapting the reference value range based on the stored reference value.

17. A storage device of a server device comprising a program code that when executed by an analysis and control unit of the server device, causes the analysis and control unit to perform operations comprising:
determining a value of a vitality parameter based on a breathing movement signal and a driving movement signal by normalizing a value described by the breathing movement signal based on a value of the driving movement signal, wherein the vitality parameter describes breathing of a user;
ascertaining a reference value range in which the determined value of the vitality parameter lies, wherein the reference value range comprises user-specific reference values of the vitality parameter that are stored in the storage device;
ascertaining a driver state index describing a current physiological state of the user based on the ascertained reference value range;
generating a control signal for operating a driver assistance device of a motor vehicle based on the ascertained driver state index; and
transmitting the control signal to the driver assistance device.

18. The storage device of claim 17, wherein the operations further comprise:
ascertaining an identity of the user;

providing the user-specific reference values of the vitality parameter; and ascertaining the reference value range based on the ascertained identity.

19. The storage device of claim 17, wherein the operations further comprise:

receiving a vitality parameter signal that describes the value of the vitality parameter or a value of another vitality parameter from a portable accessory or a mobile terminal; and wherein the ascertaining the driver state index further comprises ascertaining the driver state index based on the received vitality parameter signal.

20. The storage device of claim 17, wherein the operations further comprise:

receiving an operating signal from a motor vehicle system, wherein the operating signal describes an operating state of the motor vehicle system; and wherein the ascertaining the driver state index further comprises ascertaining the driver state index based on the received operating signal.

21. The storage device of claim 17, wherein the operations further comprise:

storing the determined value of the vitality parameter as a reference value in the storage device; and adapting the reference value range based on the stored reference value.

* * * * *